United States Patent [19]

Schryver et al.

[11] Patent Number: 5,314,487
[45] Date of Patent: May 24, 1994

[54] ACETABULAR PROSTHESIS WITH ANCHORING PEGS

[75] Inventors: Jeff Schryver, Cordova; Jeff Shea, Memphis; Dawn M. Ryan, Memphis, all of Tenn.

[73] Assignee: Smith & Nephew Richards Inc., Memphis, Tenn.

[21] Appl. No.: 830,243

[22] Filed: Feb. 10, 1992

Related U.S. Application Data

[63] Continuation-in-part of Ser. No. 656,247, Feb. 14, 1991, Pat. No. 5,226,917.

[51] Int. Cl.$^5$ .............................................. A61F 2/34
[52] U.S. Cl. .................................................... 623/22
[58] Field of Search ..................... 623/16, 18, 22, 23

[56] References Cited

U.S. PATENT DOCUMENTS

| | | | |
|---|---|---|---|
| 3,939,497 | 2/1976 | Heimke et al. | 3/1.912 |
| 4,013,071 | 3/1977 | Rosenberg | 623/16 |
| 4,563,778 | 1/1986 | Roche et al. | 623/22 |
| 4,566,138 | 1/1986 | Lewis et al. | 623/22 |
| 4,653,487 | 3/1987 | Maale | 686/94 |
| 4,685,923 | 8/1987 | Mathys | 623/22 |
| 4,792,337 | 12/1988 | Müller | 623/22 |
| 4,828,565 | 5/1989 | Duthoit et al. | 623/22 |
| 4,923,473 | 5/1990 | Griss et al. | 623/22 |
| 4,955,325 | 9/1990 | Zarnowski et al. | 623/22 |
| 4,955,917 | 9/1990 | Karpf | 623/22 |
| 4,990,161 | 2/1991 | Kampner | 623/22 |

FOREIGN PATENT DOCUMENTS

| | | | |
|---|---|---|---|
| 0013863 | 1/1979 | European Pat. Off. | A61F 1/00 |
| 0169978 | 4/1985 | European Pat. Off. | A61F 2/34 |
| 0211169 | 5/1986 | European Pat. Off. | A61F 2/34 |
| 0212087 | 5/1986 | European Pat. Off. | A61F 2/30 |
| 0341198 | 3/1989 | European Pat. Off. | A61F 2/34 |
| 2318459 | 10/1974 | Fed. Rep. of Germany | 673/22 |
| 2638963 | 5/1990 | France | 623/22 |
| 2651996 | 3/1991 | France | 623/22 |
| 9107932 | 6/1991 | PCT Int'l Appl. | |
| 1170295 | 11/1969 | United Kingdom | A61F 1/00 |
| 2080118A | 2/1982 | United Kingdom | A61F 1/03 |

OTHER PUBLICATIONS

BIAS TM Acetabular Components, Zimmer, *U.S. Pat. No. 3,605,123.
Discover Brochure.
Depuy Duraloc Cup 52 MM Photographs (2).
Depuy Profile Cup 60 MM Photographs (2).
Howmedica PCA Cup 46 MM Photographs (2).
Joint Medical Authropor II Porous Coated cup With Pegs 54 MM Photographs (2).
Joint Medical Authropor II Porous Coated Cup 54 MM Photographs (2).
Zimmer HG Porous Cup 58 MM Photographs (2).
Zimmer Ti-Bac Cup 48 MM Photographs (2).
Osteonics PSL OMNIFIT Cup 52 MM Photographs (2).
Protek Protasul Ti Cup 52 MM Photographs (2).

Primary Examiner—David Isabella
Attorney, Agent, or Firm—Pravel, Hewitt, Kimball & Krieger

[57] ABSTRACT

An improved acetabular cup prosthesis has a cup body with a plurality of bores extending between an inner concave surface and an outer convex surface, wherein the bores can function as drill guides for providing alignment in the drilling of surgical openings after the acetabular cup body is placed in a patient. A plurality of pegs or spikes have proximate end portions that have connection members for forming connections with the bores, and distal end portions that can register into the drilled surgical openings.

12 Claims, 10 Drawing Sheets

 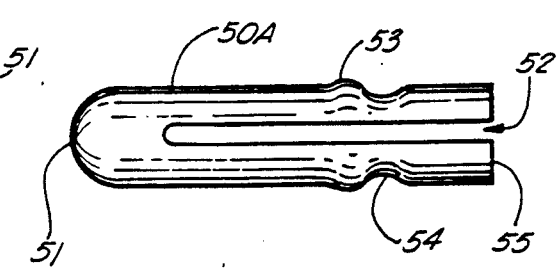 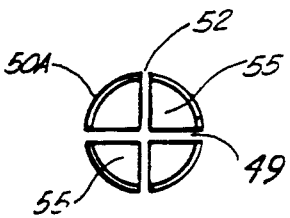
FIG. 5A     FIG. 5B     FIG. 5C
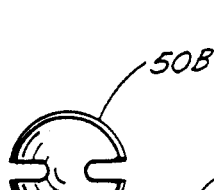 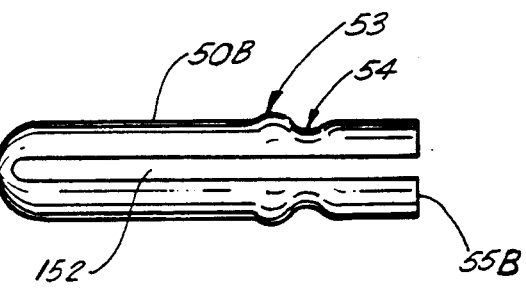 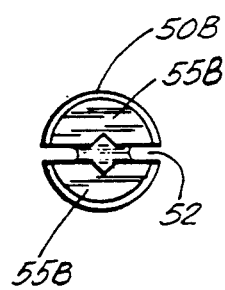
FIG. 6A     FIG. 6B     FIG. 6C
 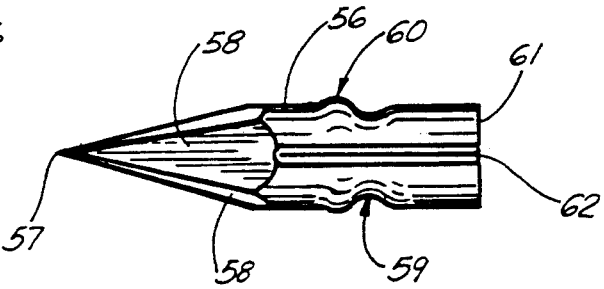 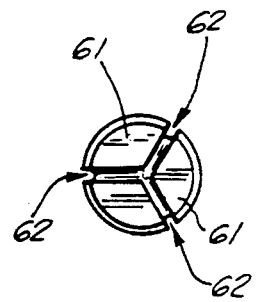
FIG. 7A     FIG. 7B     FIG. 7C

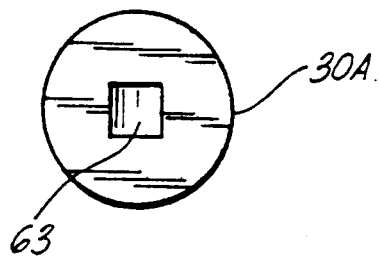
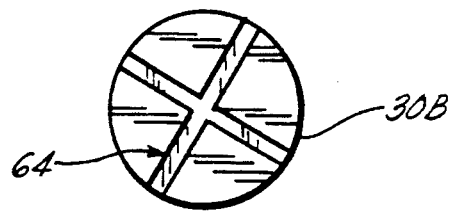
FIG. 12A  FIG. 12B
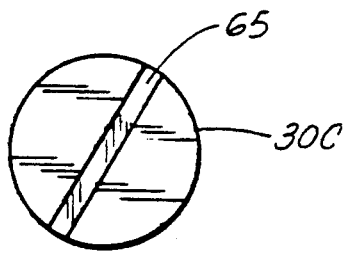
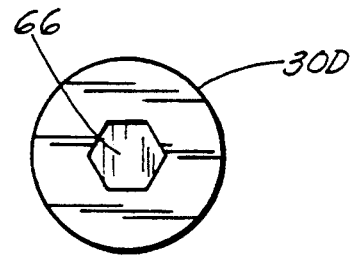
FIG. 12C  FIG. 12D
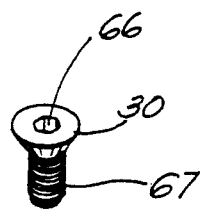
FIG. 13
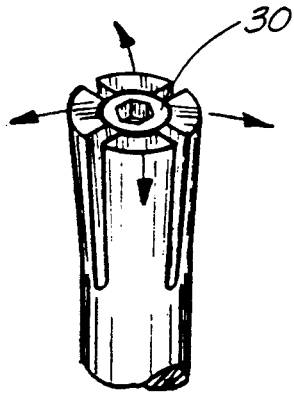
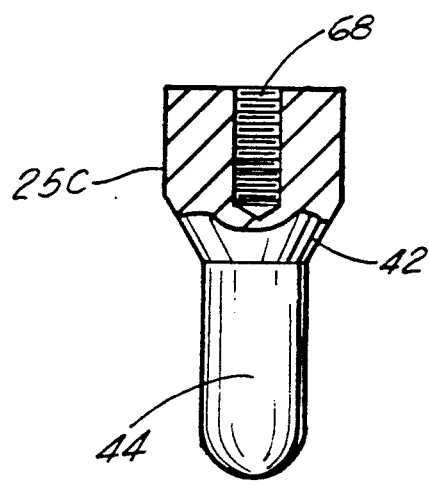
FIG. 14  FIG. 15

ACETABULAR PROSTHESIS WITH ANCHORING PEGS

This is a continuation-in-part application of prior, co-pending U.S. patent application Ser. No. 07/656,247, filed Feb. 14, 1991, now U.S. Pat. No. 5,226,917 and incorporated herein by reference.

BACKGROUND OF THE INVENTION

1. Field Of The Invention

The present invention relates to acetabular prosthetic devices and more particularly to an improved acetabular prosthesis (and method of surgically implanting), wherein the prosthesis has a cup or shell that includes radially extending bores therethrough that can be used as drill guides by a surgeon after the acetabular cup or shell has been placed in the patient's acetabulum. Holes can be drilled surgically into the underlying bone tissue using the drill guide openings so that one or more pegs for improved anchoring can be placed into the bores and affixed rigidly to the acetabular cup using an interference or wedge fit. The prosthesis (including cup or shell and rigidly affixed pegs) is thus anchored into the underlying surgical openings. The cup has a shiny polished inner, concave surface that faces the liner so that relative motion between the liner and shell will generate minimal liner debris. The polished shell concave surface has a roughness of less that sixteen micro inches.

2. General Background

There are a number of commercially available acetabular prosthetic devices that include a cup shaped body, some of which have projections extending from the outer surface of the cup-shaped body. For example, U.S. Pat. No. 3,939,497 describes a socket for a hip joint prosthesis which is secured to a cavity in the bone tissue by a series of radially arranged pegs which can be projected outwardly from the wall of the socket into the surrounding tissue by a central screw which also has a self-tapping thread that enters the tissue.

U.S. Pat. No. 4,685,923 provides a hip joint socket made from a plastics material that can be installed without the use of bone cement or adhesive. The socket comprises a hemisphere of polyethylene. The socket may have four bores extending skewed to the equatorial plane to permit the surgeon to fix the socket in the acetabulum by means of screws or dowels temporarily or permanently. The primary anchoring is provided by two plugs or pins arranged on the outer surface of a socket. The pins may be substantially parallel to each other. The pins are inserted in bore holes drilled into the bone. The bore holes are drilled so that the pins are inserted under stress. A secondary anchor in the form of flaps are present near the actuarial plane of the socket. These flaps supplement the anchoring affect of the pins.

In U.S. Pat. No. 4,792,337 an acetabular cup is provided which has a metallic anchoring shell. The cup is for cement-less fixation in the acetabulum. The shell has several holes through which screws are driven into the bone. The screws have rounded heads and the holes are countersunk so that the orientation of the screws may be varied with respect to the cup and each other.

In U.S. Pat. No. 4,828,565 there is provided a cotyliodal component for a non-cemented hip prosthesis. The component has two parts, a titanium hemispherical shell and a cup of polymer which is engaged into it. The shell has two zones, the first zone is covered with porous titanium capable of being invaded by spongy bone and also has two projecting pieces. The other zone has a smooth metal surface. Two screws pass through the projecting pieces and are used to anchor the component in the acetabulum.

Another acetabular cup for cement-less fixation in the acetabulum is described in European Patent Application No. 13,863, published Jun. 8, 1980. The cup is anchored to the bone by a central pin and a number of other pins distributed over the surface of the cup. The pins have several sawtooth notches along their length. The bone may be pre-drilled to take the pins.

European Patent Application No. 169,978 published May 2, 1986, describes an acetabular cup which has an outer shell embedded into the patient's pelvis. The outer shell has a frustro-conical skirt and a spherical central cap. The shell has a number of small tufts with rounded ends projecting from its surface. The tufts are embedded in the bone tissue to provide improved anchorage.

In European Patent Application No. 211,169 published Feb. 25, 1987, an acetabular cup is described in which an external boss protrudes from the outer surface of the acetabulum body to fit into a pre-drilled hole in the acetabulum. The cup also has two anchoring lugs in the meridian plane. The lugs take screws to aid in anchoring the cup.

Other foreign patents and patent applications which describe acetabular cups include European Patent Application No. 212,087 published Apr. 3, 1987, wherein metallic pins project from the surface of the cup and contain holes in which tissue may grow. In European Patent No. 341,198 published Nov. 8, 1989, an acetabular cup has a metal outer shell and a plastic body for retaining the hip joint head. The shell is frustro-conical in cross-section with an opening at an apex and circular teeth around the outside. Three or more anchoring dowels parallel to the convexes protrude from the outer surface of the shells. The dowels are slotted and provide with circular teeth of a sawtooth cross-section over the portions which protrude. A central bolt may be fitted into the dowel to provide a rounded end.

The use of cement for fixation of acetabular process, and in some cases the use of spacers, is found in U.S. Pat. Nos. 4,563,778, and 4,566,138. This concept of the use of bone cement and spacers is also seen in United Kingdom Patent Nos. 1,170,295 and 2,080,118.

U.S. Pat. No. 4,923,473, issued to Peter Griss et al., entitled "Hemispherical Acetabulum", relates to a hemispherical acetabulum having a fixing pin which projects from the outside surface of the acetabulum.

In prior art acetabular cup prosthetic devices, the projections or spacers are often for the sole purpose of providing a space from the bone tissue that can be occupied by bone cement. Further, many acetabular cup prosthetic devices carry projections on their outer surface which are a part of the prosthesis as constructed and which cannot be added thereafter such as during surgery.

Still other prosthetic devices in the form of acetabular cups provide pegs which must be affixed to the tissue before the acetabular cup is placed in the position. Pegs which are preattached to the cup may require predrilling or other preparation which includes impaction for the purpose of forcing the projections into the bone. The bone bed may require advance preparation in some devices to accept the protrusions.

SUMMARY OF THE PRESENT INVENTION

The present invention provides an improved acetabular cup prosthesis wherein the prosthesis body (i.e. cup or shell) with pegs having attachment to the cup. The cup preferably includes openings therethrough which can function as drill guides for the surgeon after the cup has been placed in the patient's acetabulum. The present invention affords improved fixation and stability of the component because pegs can be placed in the acetabular cup after it has been placed in position by the surgeon. The pegs can be easily installed from the concave side of the acetabular cup component notwithstanding the fact that the acetabular cup component has already been placed in operative position in the patient's acetabulum.

With the present invention, a multiplicity of pegs can be rigidly attached to the acetabular cup prosthesis body for the purpose of securing it in place in the acetabular bone. This can be done through an opening or bore which is interchangeably used for a desired peg.

With the present invention, the acetabular cup can be placed in it's desired position in the acetabulum by the surgeon. The pegs (as described more fully herein) are then added to the cup body and attached to the prosthesis in a rigid fashion. Each peg protrudes through the acetabular cup body and into the underlying bone tissue of the acetabulum to provide a mechanical locking of the acetabular cup (including pegs) into the pelvis. The surgeon can use a pre-drill before placing the peg or spike wherein the opening or bore in the acetabular cup body functions as a drill guide. Pegs can be selectively placed so that they are not aligned with each other but are at angles to each other which aids in the mechanical stability of the acetabular cup body.

The apparatus preferably uses a plurality of pegs that feature a taper or wedge lock, barb lock, or knurl lock, to form an interference fit, or compression friction lock, and a rigid connection with the aetabular cup at the drill guide openings. The interference fit assures a rigid connection between peg and cup body so that each peg and cup body move together, rather that relative to one another. Relative motion causes possible contact between a peg and any polymer liner, creating the problem of liner debris generation. The pegs are smooth along the distal portion thereof so that movement of the peg and cup as a unit will not disrupt adjacent bone tissue.

The present invention thus provides an improved acetabular cup prosthesis that includes an acetabular cup body or shell component, having an inner concave surface and an outer convex surface.

A plurality of openings extend between the inner and outer surfaces along radial lines that can merge substantially near a center of curvature of the inner concave surface of the cup body, the openings forming elongated bores surrounded by a bore wall portion of the acetabular cup body. The cup body or shell can be spherical in form, or not spherical in form (such as e.g., an egg-shaped cup or shell).

The plurality of openings are positioned to define drill guides so that during a surgical implantation of the prosthesis, the surgeon can selectively drill into the underlying tissue through one or more of the openings and form surgical openings therein in the underlying bone tissue.

There are preferably a plurality of peg members, each being insertable into and registering with one or more of the openings in the prosthesis body, the peg members having a first proximate end portion having means thereon for forming a rigid connection with the acetabular cup body at one of the openings and with the bore wall, and a second smooth distal end portion adapted to extend into the underlying tissue (e.g., into surgically formed openings) after the cup body has been implanted in a patient.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIGS. 5A–5C are bottom, side, and top views of peg portion of the first embodiment of the apparatus of the present invention;

FIGS. 6A–6C are bottom, side, and top views of another peg as used with the first embodiment of the apparatus of the present invention;

FIGS. 7A–7C are bottom, side, and top views of a spike member as used with the first embodiment of the apparatus of the present invention;

FIGS. 12A–12D are top views of locking pin members used with the taper locking embodiment of the spike;

FIG. 13 is a perspective fragmentary view of the first embodiment of the apparatus of the present invention illustrating the peg locking screw portion thereof;

FIG. 14 is a perspective fragmentary view illustrating an interface of the peg locking screw with one of the pegs of FIGS. 5A–5C;

FIG. 15 is a partial sectional view illustrating the peg of FIG. 10;

FIG. 22 is a fragmentary sectional view of the second embodiment of the apparatus of the present invention illustrating the cup and cup liner connection.

DETAILED DESCRIPTION OF THE PREFERRED EMBODIMENT

Figure 1:
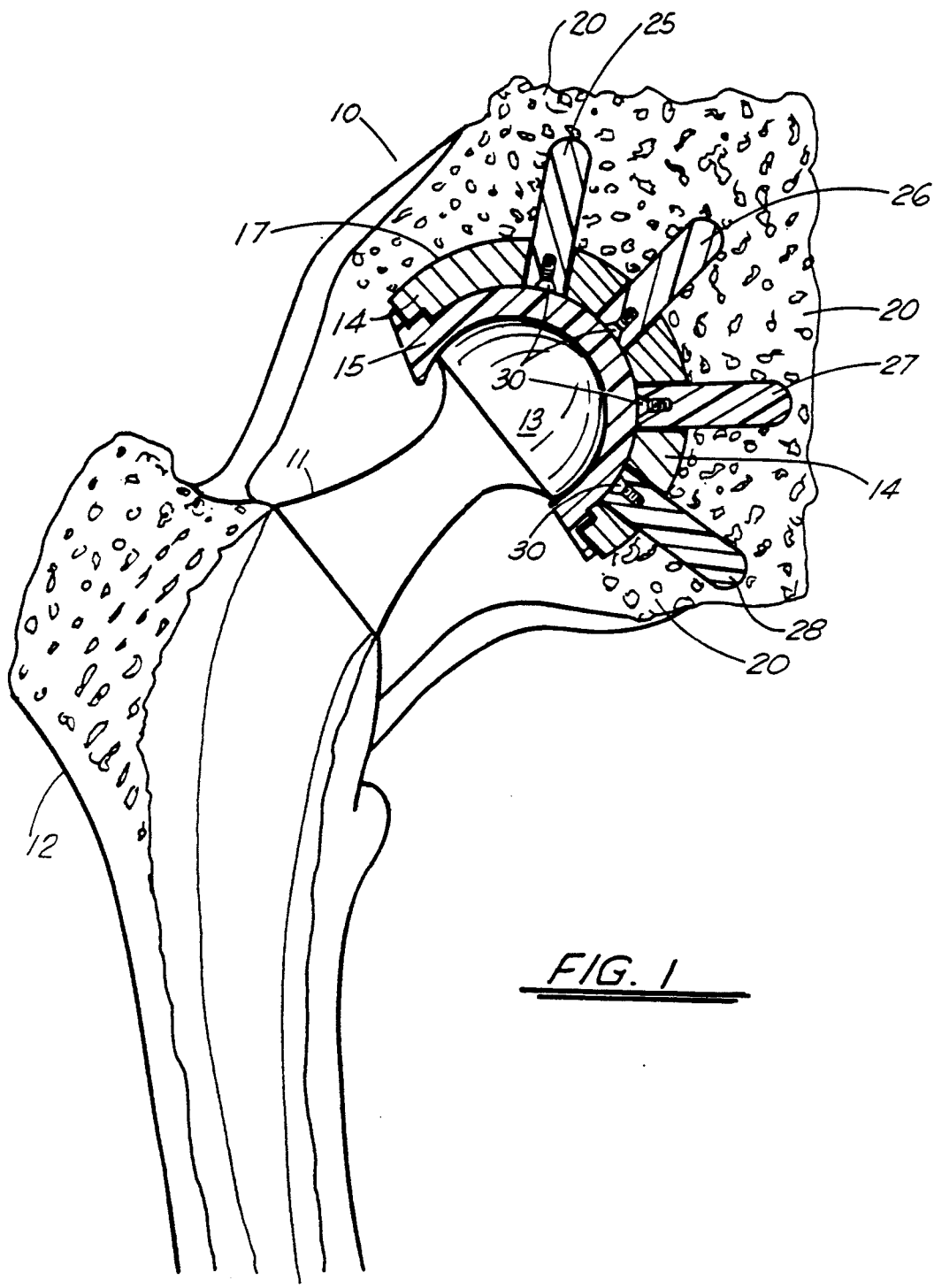
FIG. 1 is a side sectional view of a first embodiment of the apparatus of the present invention.
Figure 2:
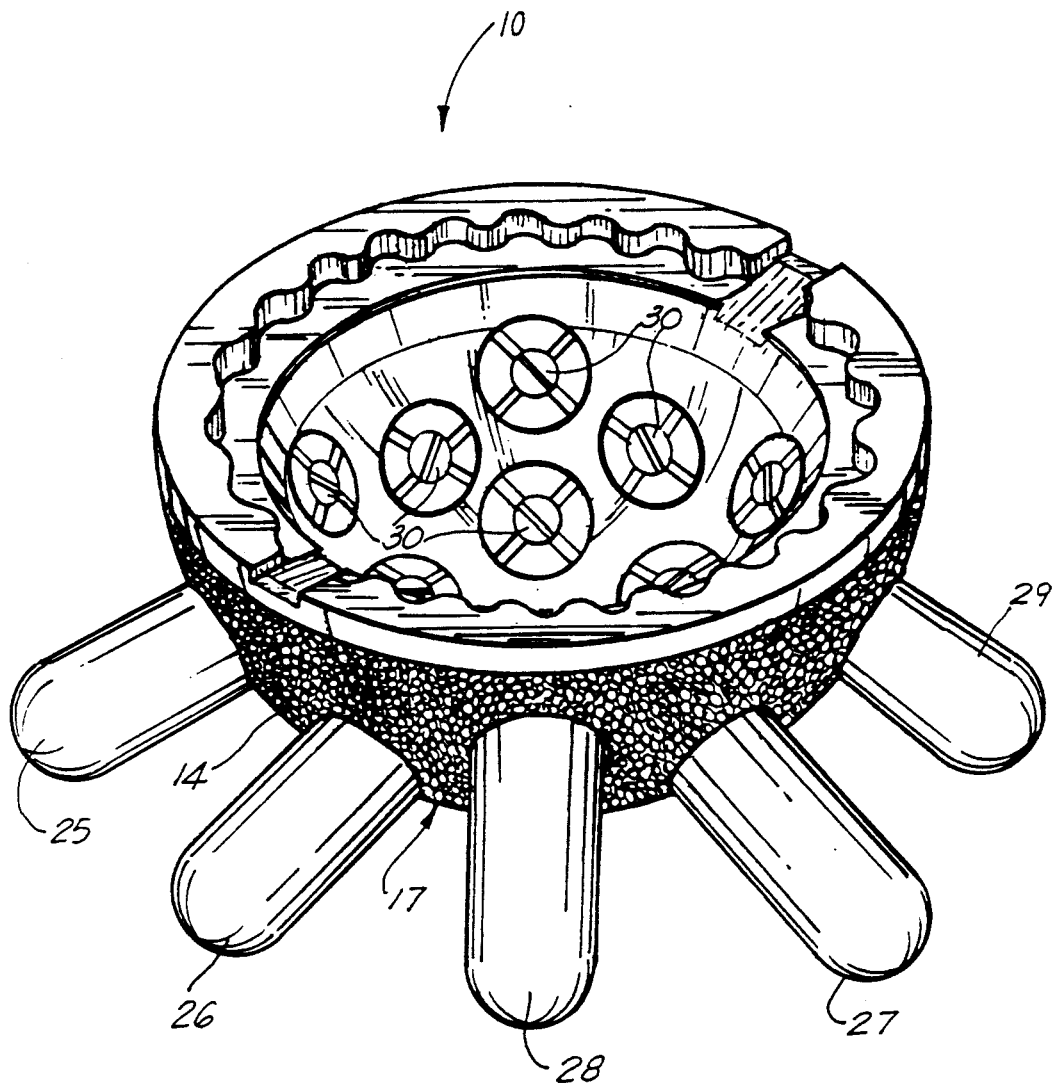
FIG. 2 is a perspective view of the first embodiment of the apparatus of the present invention.

In FIG. 1 there can be seen a sectional view of the first embodiment of the apparatus of the present invention designated generally by the numeral 10. In FIG. 1, there can be seen a hip prosthesis member 11 mounted in a femur 12 of a patient. The hip prosthesis 11 includes an upper ball portion 13 that registers with the acetabular prosthetic apparatus 10 of the present invention.

The acetabular prosthesis 10 includes a cup or shell prosthesis body 14, preferably of a metallic material with a plastic liner 15 portion. The metallic cup body 14 includes an inner concave surface 16 and an outer convex surface 17. The surfaces 16, 17 are spaced apart, defining the thickness of the cup or shell 14.

Figure 3:
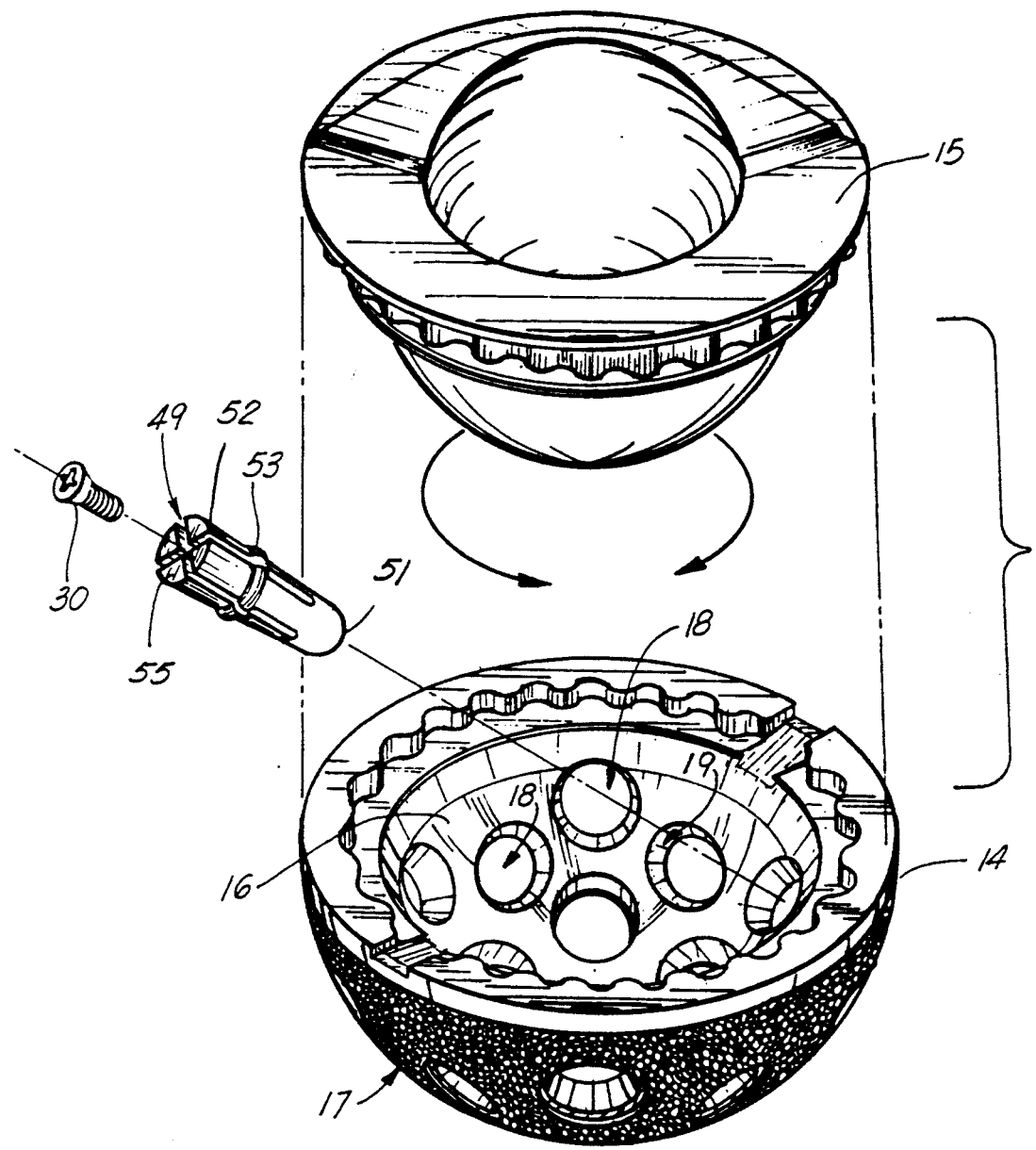
FIG. 3 is an exploded perspective view of the first embodiment of the apparatus of the present invention.

A plurality of openings 18 in form of preferably elongated bores extend between the inner concave surface 16 and the outer convex surface 17. These openings are in the form of bores having a bore wall 19 as seen in FIG. 3. The openings 18 can function as drill guides for the surgeon. Therefore, once the metallic cup body 14 portion of the acetabular cup prosthesis 10 is placed in position in the patient's acetabulum as shown in FIG. 1, the surgeon can simply drill through any one of the plurality of bores forming an opening in the underlying bone tissue designated generally be the numeral 20.

When the surgeon places the cup body 14 in the position shown in FIG. 1, the plurality of bores 18 can act as a drill guide for the surgeon. The bore 19 walls of each opening 18 define a cylindrically shaped guide for a correspondingly sized drill. These openings allow the surgeon to form surgical openings in the underlying bone tissue 20.

A selected surgically formed opening 18 is then occupied by a peg (and not necessarily each opening 18), such as one of the pegs 25-29, as seen in FIGS. 1-3 and 4A. In the preferred embodiment, each of the pegs 25-29 extends into the bone tissue at a different angular position with respect to the other pegs to provide a rigid anchor for the cup 14. Pegs 25-29 can be polymer, metal, or resorbable polymer.

Once the pegs 25-28 are placed into operative position, a strong connection is formed between the outer surface of each peg 25-28 and the walls 19 of each opening or bore 18. In FIGS. 5A-5C, 6A-6C, 7A-7C, and 8-11, various embodiments of the pegs, their respective attachments to the cup body 14 are illustrated.

Figure 8:
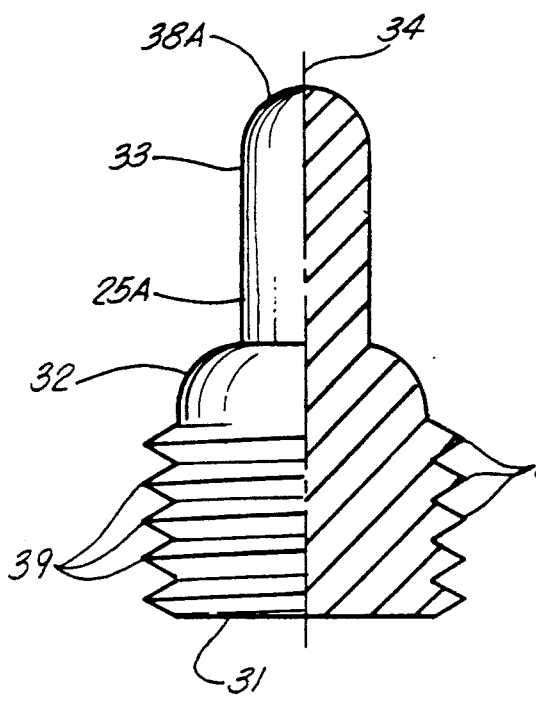
FIGS. 8, 9, 10, and 11 are peg members used with the first embodiment of the apparatus of the present invention including respectively thread lock, barb lock, taper lock, and knurl lock embodiments thereof.

In FIG. 8, peg 25A includes a proximate end portion 31 and a distal end portion 38A and a central longitudinal axis 34. A smaller diameter section 33 connects with a larger diameter section 32 that is covered with an external spiralling thread 39. The thread 39 bites into and interfaces with the cup body 14 at the wall 19 of each opening 18. The opening or bore 18 wall 19 can also be internally threaded to engage the thread 39.

Figure 9:
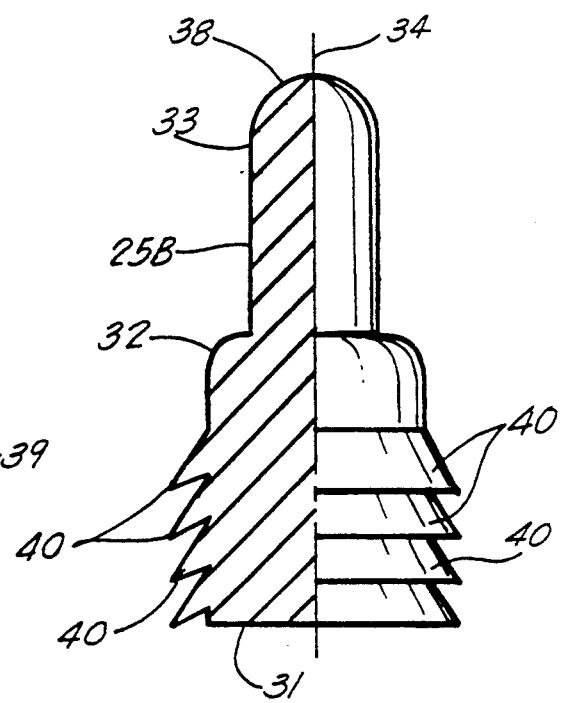

In FIG. 9, peg 25B is provided with a proximate end 31, a distal end 34, a smaller diameter section 33, and a larger diameter section 32 that carries a plurality of annular barb rings 40. When the peg 25B is forced into the opening 18, the barbs 40 form a tight fit with the cup body 14 at the wall 19 of each opening 18.

Figure 10:
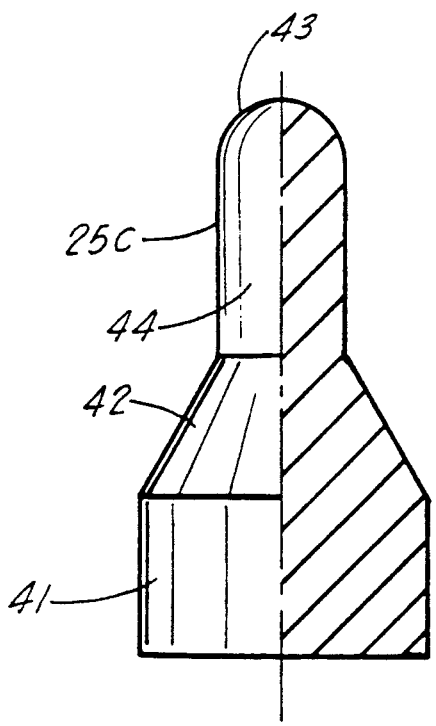
Figure 11:
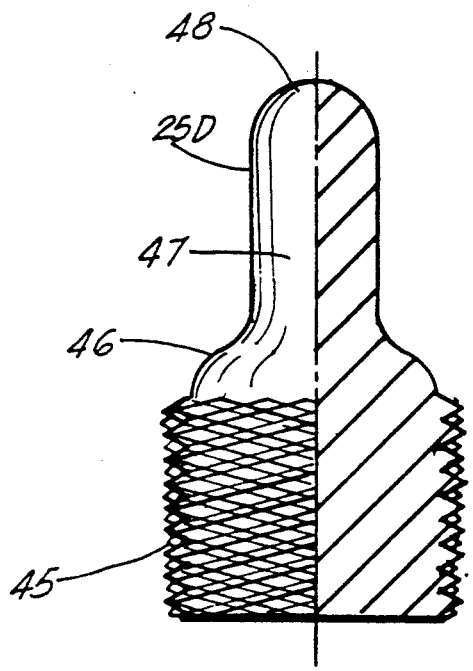
Figure 16:
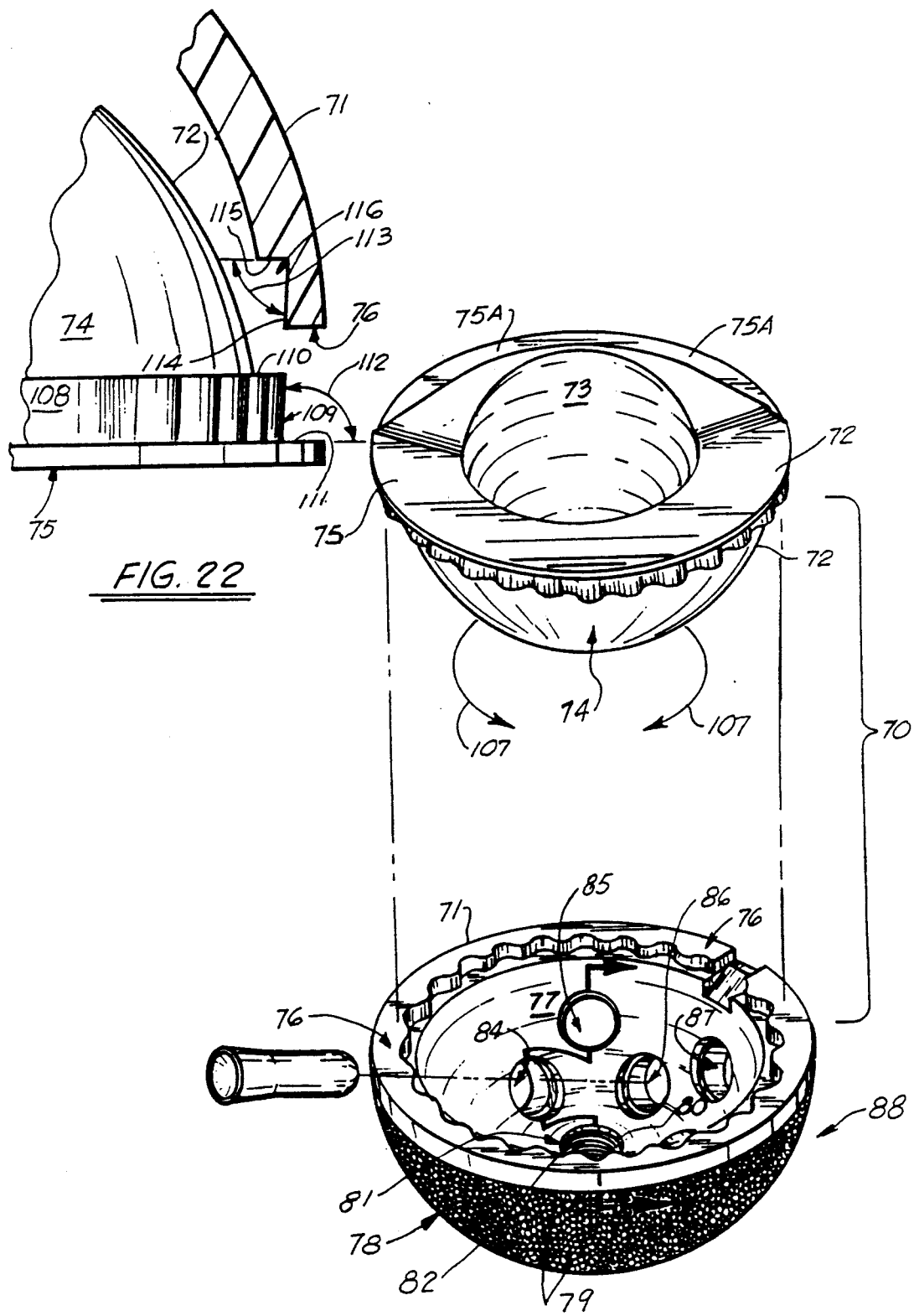
FIG. 16 is a perspective view of a second and preferred embodiment of the apparatus of the present invention.
Figure 17:
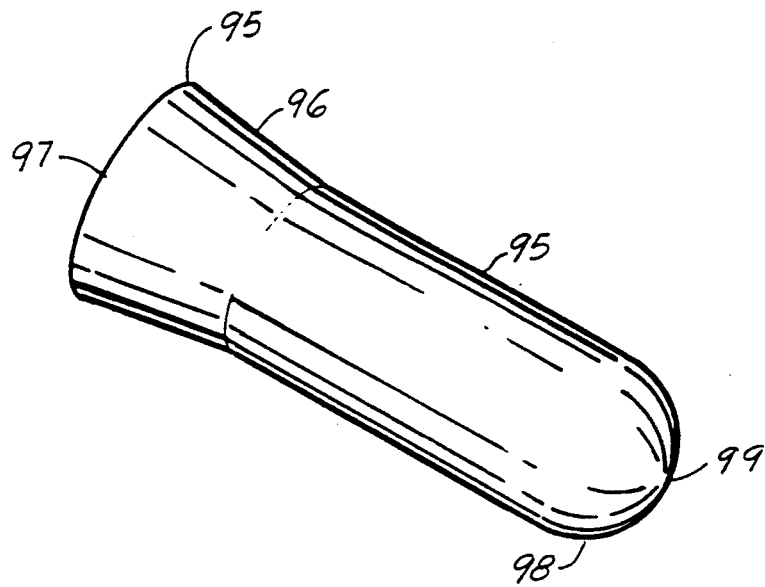
FIG. 17 is a fragmentary view illustrating a peg member used with the second embodiment of the apparatus of the present invention.

In the embodiment of FIGS. 10, 11, and 15, pegs 25C, 25D provide a proximate, larger diameter 41 end portion, a smaller generally cylindrical distal end portion 44, and a transitional frustro-conical section 42, and a curved end 43. Similarly, peg 25D has a proximate, larger diameter 45 portion, a curved annular transition section 46, a smaller and generally cylindrical section 47, and a curved end portion 48.

The large diameter section 41 and the frustro-conical portion 42 can also be seen in FIG. 15 in a partial sectional view. The larger diameter and frustro-conical sections 41, 42 surround an internally threaded bore 68 which accepts set screw 30. The screw 30 is sized to expand the enlarged 41 and frustro-conical 42 sections slightly when the peg 25C is placed in position within one of the bores 18 which would be similar in shape to the outside surface of frustro-conical portion 42 and enlarged portion 41.

When the set screw 30 is fully threaded into the threaded opening 68, so that the external thread 67 of the set screw 30 engages the internal thread 68 of the bore, a taper lock connection or interference fit is formed between the peg 25C and the wall 19 of opening 18. Internal threads 68 in FIG. 15 can also be used as an extraction or holding means for placing and removing the peg 25c. Peg 25c would be used then without a screw 30.

The set screw 30 can have different tooled sockets, as shown in FIGS. 12A-12D. In FIG. 12A, a set screw 30A includes a square tooled socket 63. In FIG. 12B, the set screw 30B has a X-shaped slot 64 for receiving a Phillips-type screwdriver, for example. In FIG. 12C, the set screw 30C has a single transverse slot 65 and in the embodiment of FIG. 12B, the set screw 30B has an hexagonal tool socket 66. Other tooled sockets could be employed.

Figure 4A:
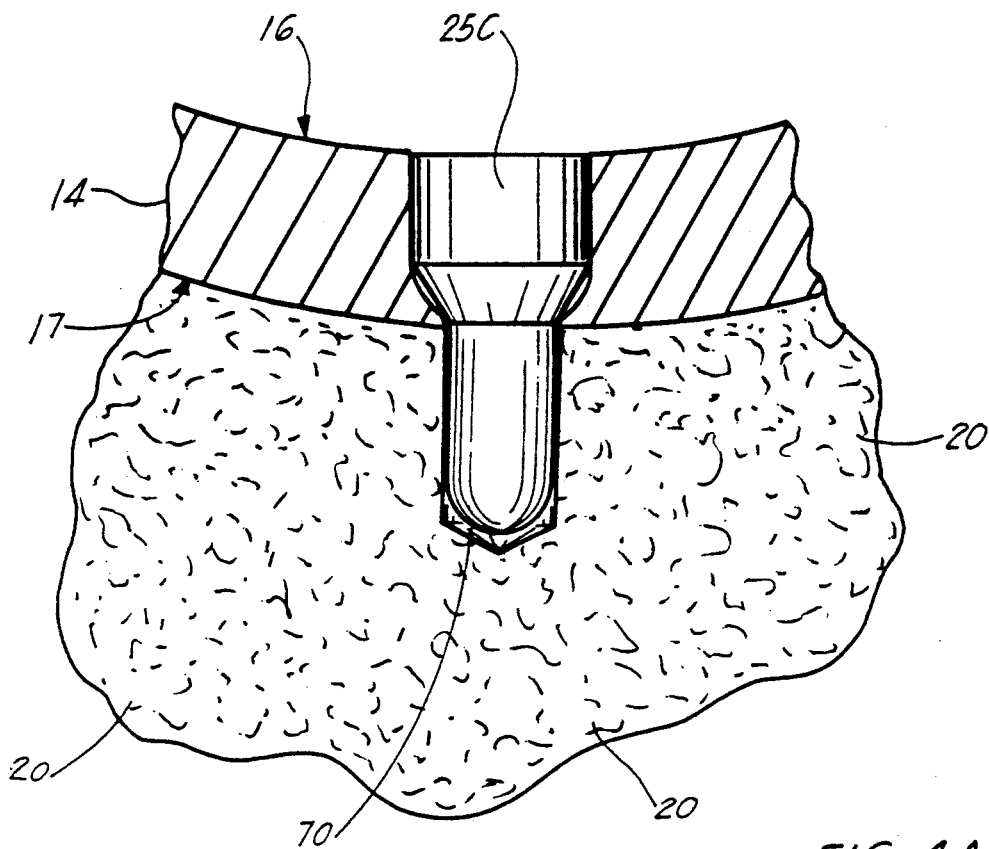
FIGS. 4–4A are fragmentary views of the first embodiment of the apparatus of the present invention.
Figure 4:
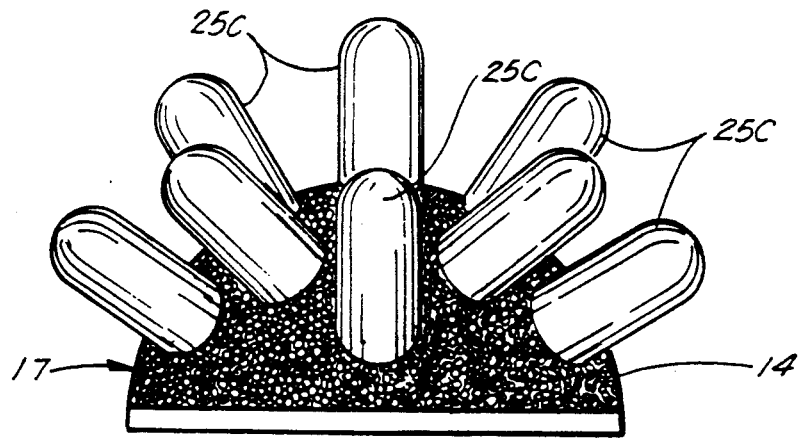

In FIGS. 4-4A, the pegs 25C can be shown extending from the convex 17 surface of cup body 14 and into a surgically formed opening 70 which is formed by the drill that penetrates the opening 18. In such a situation, the surgeon simply uses the opening 18 as a drill guide for a similarly shaped drill when forming surgical opening 70.

In FIGS. 5A-5C, an alternate construction of the peg is illustrated, designated generally by the numeral 50A. Peg 50A includes a rounded or hemispherical distal end portion 51 and a proximate end portion 52 that includes a pair of longitudinally extending slots 49, forming four peg sections 55.

In the embodiments of FIGS. 6A-6C, the peg 50B provides a hemispherical distal tip 51 and a single longitudinally extending transverse slot 152 forming two peg sections 55B. Enlarged annular shoulder 53 and smaller diameter recess 54 are also provided in each of the embodiments of FIGS. 5A-5C and 6A-6C.

In the embodiment of FIGS. 7A-7C, a spike-shaped peg 56 is provided having a pointed tip portion 57, and a plurality of beveled surfaces 58 that connect with a cylindrical peg body portion that includes an enlarged annular section 60 and a smaller diameter constricted section 59. The proximate 61 end portion of the peg includes a longitudinally extending Y-shaped slot 62, as seen in FIGS. 7B and 7C.

FIGS. 16-22 illustrate a second and preferred embodiment of the apparatus of the present invention designated generally by the numeral 70. Acetabular cup apparatus 70 includes a cup body 71 to which can be removably affixed a plastic cup liner 72 made of polyethylene for example. Liner 72 has an inner concave surface 73 and an external convex surface 74. Liner 72 is in the form of a hemispherical member having an annular base 75 with a plurality of curved members extending around the periphery of liner 72 at base 75 and which interface with a similarly shaped circumferentially recess formed on cup body 71 to prevent rotation of liner 72 with respect to body 71.

The cup body 71 is preferably metallic having an annular base 76 that defines a plane. The cup body 71 has an inner concave surface 77 and an external convex surface 78. The cup body 71 concave surface 77 is a shiny polished surface that faces the convex surface 74 of polymeric liner 72. The polished concave surface 77 has a roughness of less than sixteen (16) microinches, and preferably about eight (8) microinches. Such a highly polished surface 77 appears mirror-like. The polished concave surface 77 inhibits polymer liner debris generation.

External surface 78 can be covered with a plurality of small metallic beads or the like forming a bone ingrowth surface 79. The apex 80 of cup body 71 has a through opening 81 that has an internal thread 82 for attachment thereto of a tool for inserting and/or removing the cup body 71 from its position in the acetabular bone tissue of a patient.

Figure 20:
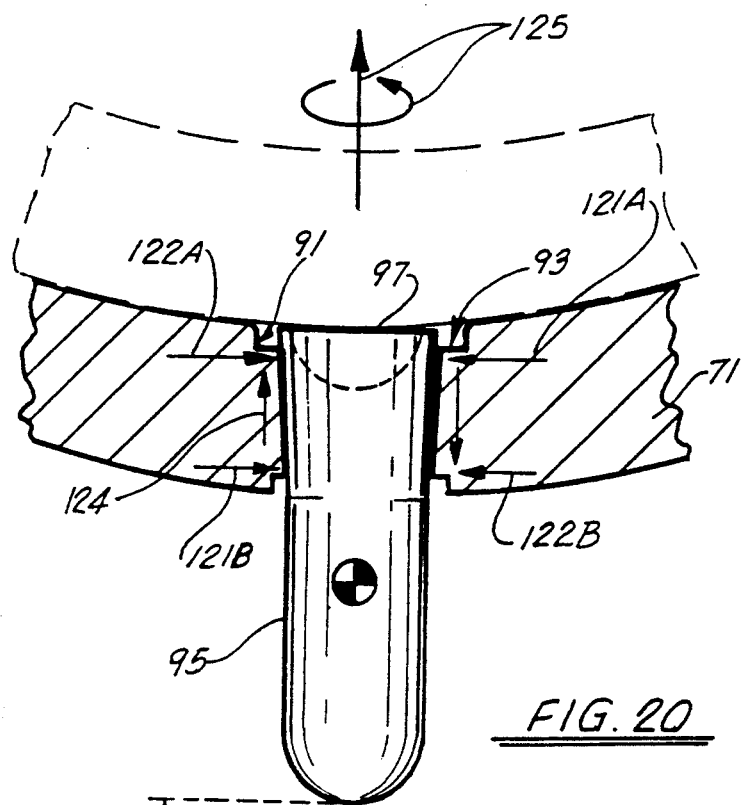
FIG. 20 is a another fragmentary sectional view illustrating the second embodiment of the apparatus of the present invention.
Figure 21:
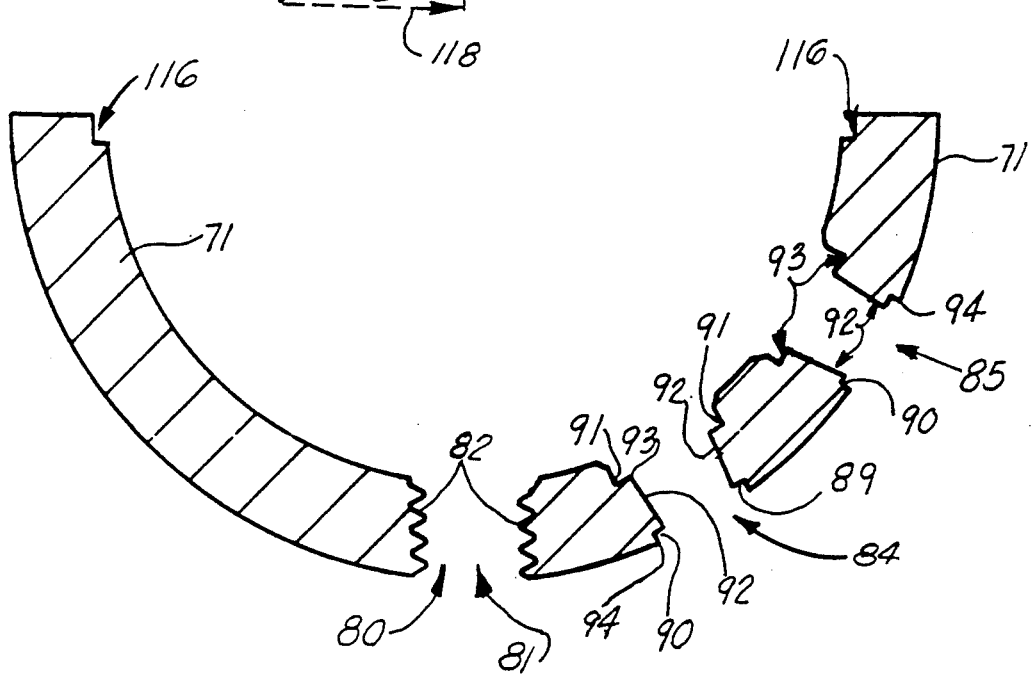
FIG. 21 is a another fragmentary sectional view illustrating the cup portion of the second embodiment of the apparatus of the present invention.

A plurality of four openings 84, 85, 86 and 87 are provided preferably in one quadrant 88 of cup body 71. Each opening 84-87 has an internal opening configuration that includes a larger diameter generally cylindrically shaped opening portion 91 and a smaller diameter opening portion 92 (FIG. 20). The larger and smaller diameter sections 91, 92 are interfaced by an annular shoulder 93. The smaller diameter section 92 can be tapered from a point of maximum diameter adjacent annular shoulder 93 to a point of minimal diameter adjacent the annular shoulder 89. A second larger diameter cylindrical section 90 meets outer edge 94 of each opening 84-87.

Pegs 95 can be selectively fitted into any one of the openings 84-87 during use. Each peg 95 has a tapered section 96 that includes a larger diameter circular base 97 defining a proximate end portion of peg 95. Distal end portion 98 of peg 95 is generally cylindrical and smooth, and includes a curved or hemispherical smooth tip 99.

In FIG. 20 force arrows are used to demonstrate that the above-described connection between each peg 95 and the cup body 71 is a substantially rigid connection that produces load transfer between each peg member and the cup body of tension loads, compression loads, axial torsion loads, and bending moment loading. Thus, the peg 95 does not rotate nor back out with respect to the opening 85-87.

The force arrow 117 is an angled force having both a bending force component (Fb) designated as 118 and a compression force component (Fc) designated as 119. The force arrows 120 and 124 show shear forces at the interface between peg 95 and cup body 71 at a selected opening 84-87. The force arrows 121A,B are force arrows that are resisting the shear forces and the force arrows 122A,B are resisting bending forces.

Figure 18:
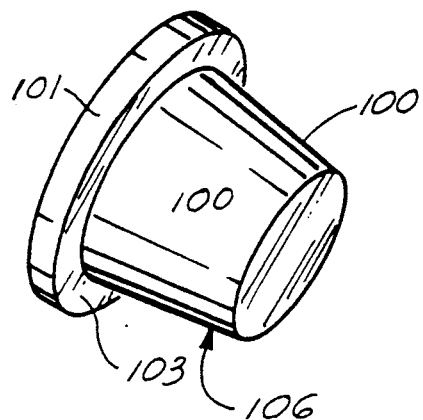
FIG. 18 is a fragmentary view illustrating the closure member portion of the second embodiment of the apparatus of the present invention.
Figure 19:
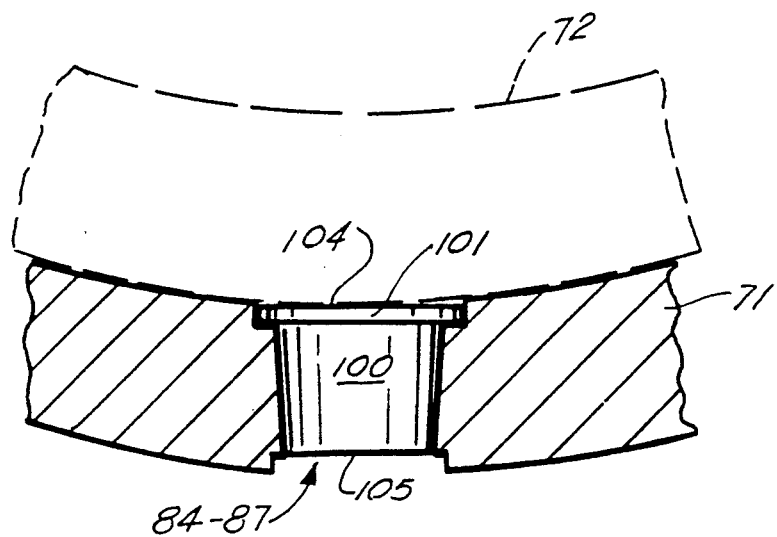
FIG. 19 is a fragmentary sectional view illustrating the second embodiment of the apparatus of the present invention.

A closure member 100 is shown in FIGS. 18-19 and includes a larger section 101 and a smaller diameter section 102. Annular shoulder 103 forms an interface between the larger 101 and smaller 102 diameter sections. Closure member 101 has an enlarged circular base 104 defining its proximate end portion during use and a smaller circular flat distal end 105.

The larger diameter section 101 of closure member 100 can have a beveled annular wall 106 for forming a wedge type fit with the larger diameter section 91 of a particular selected opening 84-87. In this manner, the closure member 100 can be placed in any one of the selected openings 84-87 and pressed into the selected opening 84-87 by the user even after the cup body 71 has been placed into operative position. The user simply presses the closure member 100 into one of the selected openings 84-87 by accessing the cup body 71 from the concave 77 side.

The surgeon can close any one of the selected openings 84-87 using the closure member 100 after the cup body 71 has been placed in the desired operative position and anchored into position using one or more of the pegs 95. The closure member 100 may be placed in the shell 71 before implantation, such as during manufacturing, and then selectively removed by the surgeon before use of the shell 71. Each closure member 100 occupies a position in its selected opening 84-87 and between the convex 78 and concave 77 surfaces of shell or cup body 71.

Each of the openings 84-87 has a generally cylindrical smaller diameter section 92 that can act as a drill guide for the surgeon so that drilled openings can be made into the underlying bone tissue after the acetabular cup body 71 has been placed into position. This allows one or more pegs to be placed into one or more of the selected openings 84-87. Any of the selected openings 84-87 that are not selected can be plugged using the closure member 100. This prevents the flow of the polyethylene liner into any of the openings 84-87 that are not occupied by a peg 95. The closure member 100 friction fits into the above-mentioned larger diameter portion 91 of the openings 84-87.

In FIG. 22, the connection between cup 71 and liner 72 is illustrated with greater detail. Liner 72 can be rotated as shown by arrows 107 in FIG. 16 until the raised portion 75A of base 75 is in a selected position. The liner 70 is then fitted to the cup 71 by engaging the annular recess 116 of the cup 71 with the annular corrugated shoulder 108 of the liner 72. Shoulder 108 has an inclined annular shoulder that forms an acute angle of between about eighty and eighty five degrees with the flat upper surface 111 of annular base 75 of liner 72.

The surface 111 is flat so as to register with the surface of base 76 of cup 71. The numeral 112 in FIG. 22 designates the angle between surface 111 and inclined annular wall 109. A recess 116 has a corresponding shape and size to the annular corrugated shoulder 108. The angle 113 formed between inner inclined annular surface 114 and annular surface 115 is the same angular measure as angle 112.

This configuration of annular shoulder 108 and recess 116 provides a snap or interference fit between the liner shoulder 108 and the cup 71 at recess 116 which helps secure the liner 72 to the cup 71 during use.

The following Table 1 lists part numbers and corresponding par descriptions as used herein and in the drawings:

TABLE I

PARTS LIST

| PART NUMBER | PART DESCRIPTION |
|---|---|
| 10 | acetabular cup apparatus |
| 11 | hip prosthesis member |
| 12 | femur |
| 13 | ball portion |
| 14 | cup body |
| 15 | plastic liver |
| 16 | inner concave surface |
| 17 | outer convex surface |
| 18 | openings |
| 19 | bore wall |

TABLE I-continued

PARTS LIST

| PART NUMBER | PART DESCRIPTION |
| --- | --- |
| 20 | bone tissue |
| 25-29 | pegs |
| 25A-D | pegs |
| 30 | set screw |
| 31 | proximate end |
| 32 | larger diameter section |
| 33 | smaller diameter section |
| 34 | longitudinal axis |
| 38 | distal end |
| 38A | distal end |
| 39 | thread |
| 40 | annular barb rings |
| 41 | larger diameter end |
| 42 | frustro-conical section |
| 43 | curved end |
| 44 | distal end portion |
| 45 | larger diameter end |
| 46 | transition section |
| 47 | smaller diameter section |
| 48 | curved portion |
| 49 | slot |
| 50A | peg |
| 51 | hemispherical end |
| 52 | proximate end |
| 53 | annular shoulder |
| 54 | annular recess |
| 55 | peg sections |
| 56 | peg |
| 57 | pointed tip |
| 58 | beveled surface |
| 59 | smaller diameter section |
| 60 | annular shoulder |
| 61 | proximate end |
| 62 | slot |
| 70 | acetabular cup apparatus |
| 71 | cup body |
| 72 | cup liner |
| 73 | concave surface |
| 74 | convex surface |
| 75 | annular base |
| 75A | raised portion |
| 76 | annular base |
| 77 | concave surface |
| 78 | convex surface |
| 79 | bone ingrowth surface |
| 80 | apex |
| 81 | opening |
| 82 | threaded portion |
| 84 | opening |
| 85 | opening |
| 86 | opening |
| 87 | opening |
| 88 | quadrant |
| 89 | shoulder |
| 90 | larger diameter cylindrical section |
| 91 | larger diameter cylindrical section |
| 92 | smaller diameter section |
| 93 | annular shoulder |
| 94 | annular edge |
| 95 | peg |
| 96 | tapered section |
| 97 | base |
| 98 | distal end of peg |
| 99 | hemispherical tip |
| 100 | closure member |
| 101 | larger diameter section |
| 102 | smaller diameter section |
| 103 | annular shoulder |
| 104 | larger base |
| 105 | distal end of closure member |
| 106 | beveled annular wall |
| 107 | curved arrow |
| 108 | annular corrugated shoulder |
| 109 | angled annular sidewall |
| 110 | upper flat surface |
| 111 | upper surface of annular base |
| 112 | angle |
| 113 | angle |

TABLE I-continued

PARTS LIST

| PART NUMBER | PART DESCRIPTION |
| --- | --- |
| 114 | inner inclined annular surface |
| 115 | annular surface |
| 116 | annular recess |
| 117 | force arrow |
| 118 | force component, bending |
| 119 | force component, compression |
| 120 | force arrow, shear |
| 121A,B | force arrows |
| 122A,B | force arrows |
| 123 | force arrows |
| 124 | force arrow, shear |
| 125 | force arrows, torsion |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An acetabular cup prosthesis, comprising:
  a) an acetabular cup body having an inner concave surface and an outer convex surface;
  b) a plurality of openings that extend between the inner and outer surfaces, the openings forming bores surrounded by a bore wall portion of the acetabular cup body at least two of the bores have axes that are not parallel to each other;
  c) the openings being positioned to define drill guides so that the surgeon can drill into the underlying tissue and form surgical openings therein via the openings;
  d) at least one peg closure member, each being insertable into and registering respectively with one of the openings, each peg member having a first proximal end portion having means thereon for forming a substantially rigid connection with the acetabular cup body at one of the openings and with the bore wall; and
  e) wherein the closure members are disposed between the concave and convex surfaces of the cup body during use, and wherein each peg closure member has a length substantially greater than the diameter of the peg closure member for extending into and engaging the underlying bone tissue.

2. The acetabular cup prosthesis of claim 1 wherein each peg closure member has a beveled annular wall portion.

3. The acetabular cup prosthesis of claim 1 wherein the peg closure member has a first larger diameter portion and a second smaller diameter portion.

4. The acetabular cup prosthesis of claim 3 wherein the peg closure member larger diameter portion defines a proximal end portion of the peg closure member.

5. The acetabular cup prosthesis of claim 1 wherein the peg closure member includes means for forming a wedge fit with an opening.

6. The acetabular cup prosthesis of claim 1 wherein there are a plurality of peg members filling each of the plurality of openings.

7. The acetabular cup prosthesis of claim 1 wherein the inner concave surface is a highly polished surface.

8. The acetabular cup prosthesis of claim 7, further comprising:

f) a polymeric liner that fits the cup body at the inner concave surface.

9. The acetabular cup prosthesis of claim 1, further comprising:

f) a polymeric liner that fits the cup body at the inner concave surface.

10. The acetabular cup prosthesis of claim 9 wherein the polymeric liner includes corresponding inner and outer curved surfaces.

11. The acetabular cup prosthesis of claim 9 wherein the polymeric liner includes an outer convex surface and an inner concave surface.

12. The acetabular cup prosthesis of claim 1 wherein the acetabular cup body is metallic.

* * * * *